United States Patent [19]

Pulwer et al.

[11] Patent Number: 4,650,613

[45] Date of Patent: Mar. 17, 1987

[54] PROCESS FOR PREPARING N-PHOSPHONOMETHYLGLYCINE AND DERIVATIVES

[75] Inventors: Mitchell J. Pulwer, St. Louis; Van R. Gaertner, Ballwin, both of Mo.

[73] Assignee: Monsanto Company, St. Louis, Mo.

[21] Appl. No.: 687,313

[22] Filed: Dec. 28, 1984

[51] Int. Cl.$^4$ .............................................. C07F 9/38
[52] U.S. Cl. .............................. 260/502.5 F; 558/145
[58] Field of Search .......................... 260/940, 502.5 F; 558/145

[56] References Cited

U.S. PATENT DOCUMENTS 4,251,256  1/1981  Gaertner ............................ 260/940

OTHER PUBLICATIONS

Adams et al., "Organic Reactions", vol. 5, (1949), pp. 79, 109.
Kirk-Othmer Encyclopedia of Chemical Technology, 3rd Ed. (1979), No. 7, pp. 370 to 385.
Butskus et al., "Chem. Abstracts", vol. 55, (1961), 405d.
Butskus et al., "Chem. Abstracts", vol. 55, (1961), 1460f.
Denis et al., "Chem. Abstracts", vol. 55, (1961), 24583e.
Novacek, "Czech. Chem. Comm.", vol. 36, (1971), 1964–1972.

*Primary Examiner*—Anton H. Sutto
*Attorney, Agent, or Firm*—Frank D. Shearin; Raymond C. Loyer

[57] ABSTRACT

There is disclosed a process for the preparation of N-phosphonomethylglycine by dealkylation of N-alkyl-N-phosphonomethylglycine. The N-alkyl moiety contains an electron withdrawing group in the 2-position. Certain novel N-alkyl-N-phosphonomethylglycines are disclosed.

9 Claims, No Drawings

1

PROCESS FOR PREPARING N-PHOSPHONOMETHYLGLYCINE AND DERIVATIVES

This invention relates to a process for preparing N-phosphonomethylglycine (glyphosate) and derivatives thereof. More particularly, the present invention relates to an improved process for preparing glyphosate and derivatives of glyphosate and to novel N-phosphonomethyl-N-substituted glycine intermediates.

BACKGROUND OF THE INVENTION

N-Phosphonomethylglycine, known in the agricultural chemical art as glyphosate, is a highly effective and commercially important phytotoxicant. Derivatives of N-phosphonomethylglycine described herein are also known to possess phytotoxicant activity. The present invention relates to a process for preparing glyphosate by dealkylation of a substituted ethyl moiety from the imino nitrogen of N-(substituted-ethyl)-N-phosphonomethylglycine.

It is known that amine compounds can be treated with acrylonitrile to form N-(2-cyanoethyl)-amines (Bruson, *Organic Reactions*, 5, 79 (1949) and Harper, *Kirk-Othmer Encyclopedia of Chemical Technology*, 3rd edition, 7, 370 (1979)). These substituted amines can then be decyanoethylated under several different sets of conditions. For example, heating N-cyanoethylamines as high as 180° C. will give the desired amines with yields between about 28% and 61% (Butskus, *Chem. Abstr.*, 55, 405d (1961)). These amines can also be obtained by treatment with other amines or hydroxide solution. Similar reactions are described in other publications about proteins and amino acids (Denis, *Chem. Abstr.*, 55, 1460f (1961) and Denis, *Chem. Abstr.*, 55, 24583 (1961)). In another reaction, sodium methoxide is employed to decyanoethylate, but this reaction is not operative in aqueous solutions (Novacek, *Collections Czechoslovakian Chemical Communications*, 36, 1964 (1971)). There are no literature references which describe the removal of ethyl groups having electron withdrawing moieties in the 2-position other than cyanoethyl from the nitrogen atom of an amine.

SUMMARY OF THE INVENTION

It has now been discovered that certain N-(2-substituted-ethyl)-N-phosphonomethylglycine compounds, which have at least one electron withdrawing group substituted at the 2-position of the N-ethyl group, can produce glyphosate or derivatives of glyphosate when treated with acids, bases, nucleophiles, or at high temperatures in the absence of added acidic or basic reagents in aqueous reaction medium.

DETAILED DESCRIPTION OF THE INVENTION

The present invention is directed to a process for preparing glyphosate and derivatives of glyphosate of the Formula (1).

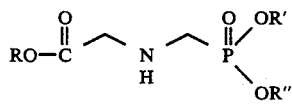

where R, R', and R" are independently selected from the group consisting of hydrogen, $C_{1-12}$ hydrocarbon groups, and herbicidally acceptable salt-forming cations.

Compounds of Formula I are prepared by dealkylation of the novel compounds of Formula II below using an acidic, basic or nucleophilic reagent or subjecting a compound of Formula II to high temperature. Compounds of Formula II are

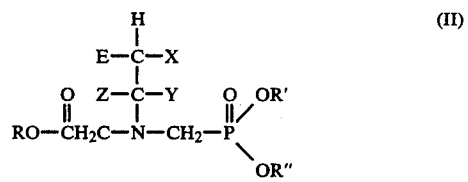

where R, R', and R" are as defined above and E is selected from the group consisting of electron withdrawing substituents; X is selected from E, hydrogen, and $C_{1-12}$ hydrocarbon groups; and Y and Z are independently selected from hydrogen and $C_{1-12}$ hydrocarbon groups.

The term $C_{1-12}$ hydrocarbon as used herein includes alkyl, alkenyl, alkynyl, aralkyl inclusive of both straight and branched chain radicals, such as methyl, ethyl, isopropyl, cyclopropyl, cyclohexyl, tertiary butyl, n-butyl, and the various forms pentyl, hexyl, heptyl, octyl, nonyl, decyl, benzyl, phenylethyl, naphthylethyl, tolylethyl, methylbenzyl, and the corresponding akenyl and alkynyl groups, aryl groups, such as phenyl, tolyl, xylyl, naphthyl, vinylphenyl and the like.

The term "aryl" as employed herein includes those groups listed above as typical aryl groups included as $C_{1-12}$ hydrocarbons.

The compounds of Formula II may be prepared by reacting an N-(2-substituted-ethyl)glycine of the following structure:

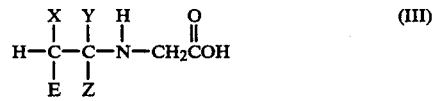

with formaldehyde and a phosphite having the following structure:

where all the substituents are as defined above in a solvent selected from the group consisting of water, lower alkanols such as methanol and ethanol, alkanes such as heptane and decane, and aromatics such as toluene or xylenes, or any combination thereof, at a temperature ranging from 0° C. to 150° C. The particular solvent used will depend upon the choice of starting materials and will therefore be readily apparent to those skilled in the art.

The term "electron withdrawing groups" is readily understood by those skilled in the art and typically include cyano, carboxyl, carboxylate anion, $C_{1-12}$ hydrocarbon carboxylate, amido, sulfinyl, sulfonyl, phosphonato, nitro and the like.

Treatment of these tertiary amino compounds of the Formula II with the appropriate acid, base, or nucleophile, or at high temperatures in the absence of added acidic or basic reagents, will then lead to the desired agriculturally useful glyphosate compounds. For example, treatment of the compound where E is carboxyl and all other substituents are hydrogen, with an aqueous solution of sodium hydroxide, leads to the trisodium salt of N-phosphonomethylglycine. Since it is known that hydroxide is either a base or a nucleophile, it is possible that the alkali in these reactions is acting as a base and/or a nucleophile. However, for the purposes of this invention, this is not important since non-nucleophilic bases such as carbonates can also be used as the reagents for the accomplishment of this reaction.

If desired, the trisodium salt of glyphosate can be converted to the free acid of glyphosate by neutralization with a proton donating source, such as mineral acid. Other salts of glyphosate can then be prepared from the neutralized product.

The product, N-phosphonomethylglycine, can also be prepared by treatment of compounds of Formula II with aqueous mineral acid.

An alternative preparation of N-phosphonomethylglycine using these N-(2-substituted-ethyl) groups involved a one-pot operation. In this case, a solution of N-(2-cyanoethyl)glycine and diethylphosphite in water was treated with formaldehyde. After removing most of the water, the residue was hydrolyzed and then treated with concentrated hydrobromic acid. The overall yield of N-phosphonomethylglycine was 76%

As a further alternative, it was possible to prepare N-phosphonomethylglycine from N-(2-substituted-ethyl)-N-phosphonomethylglycine compounds of Formula II by heating the materials in a vessel at high temperatures. These temperatures were appropriately those at which point the N-(2-substituted-ethyl) group would be cleaved giving the glyphosate product. These high temperature reactions were demonstrated by the thermolysis reaction of N-(2-cyanoethyl)-N-phosphonomethylglycine at 175° C. under vacuum. At this temperature, it was possible to distill off the by-product and to recover the desired product. Of course, the distillation of the by-product could be done so that it was recovered in a collection vessel to be reused in a further reaction. These reactions can also be done in the presence of a high boiling solvent, at elevated pressure or under vacuum. Examples of solvents which will work under vacuum are diphenylether, dodecane, sulfolane, diglyme, tetraglyme and the like. Examples of solvents which will work at elevated pressure include those listed above and others such as water, methanol, ethanol, toluene and the like. The product can then be recovered from the solvent by either crystallization, distillation of the solvent, or chromatography on an ion exchange resin. Once again the choice of particular solvents to be used is well within the skill of the ordinary chemist.

The acid reagent used to prepare glyphosate and derivatives may include hydroiodic acid, hydrobromic acid, hydrochloric acid, hydrofluoric acid, hydrogen sulfide, nitric acid, nitrous acid, perchloric acid, picric acid, phosphoric acid, phosphorous acid, pyrophosphoric acid, sulfanilic acid, sulfurous acid, sulfuric acid, and trifluoroacetic acid.

The base reagent can be selected from the group which consists of alkali metal hydroxides, alkaline earth metal hydroxides, alkali metal carbonates, alkaline earth metal carbonates, alkali metal bicarbonates, ammonia, alkyl amines, aryl amines, and alkali metal alkoxides.

The nucleophilic reagent can be selected from the list which includes any of the above base reagents which can function as nucleophiles and other compounds, for example, acetates such as sodium acetate, alkyl alcohols such as ethanol, phenols such as phenol, azides such as sodium azide, bromides such as potassium bromide, alkyl thiols such as benzyl mercaptan, aryl thiols such as thiophenol, iodides such as sodium iodide, phosphites such as triethyl phosphite, phosphines such as triphenyl phosphine, cyanides such as potassium cyanide and the like.

It is also shown that in water in the absence of the acidic, basic, or nucleophilic reagents listed above the dealkylation reaction can be induced.

The solvents for all of the reactions can be selected from the group which consists of water, lower alkanols, higher boiling ethers, such as diglyme and tetraglyme, and others which do not react with either the acidic, basic, or nucleophilic reagent or which do not decompose at high temperatures. The reactions can be run at temperatures ranging from 5° C. to 300° C. Temperatures of 50° -300° C. are preferred, especially temperatures of 90° -150° C.

The present invention thus provides a process for using novel intermediate compounds which contain a protecting group substrate, i.e., N-substituted-ethyl, which can be isolated and recycled.

In most cases it should be possible to isolate and recycle the protecting group substrate for further use. Depending on the substrate and the medium, it could be isolated by crystallization, chromatography, distillation or the like. For example, if the deprotected substrate was acrylonitrile, this compound could be recovered by distillation even as it was produced. Thus there would be no waste which is important from both an environmental and an economic viewpoint. Thus, the present invention provides a unique and advantageous method for preparing glyphosate and other glyphosate related products.

Glyphosate can be isolated by a number of methods. It was possible to chromatograph the crude reaction mixtures on ion exchange resin and thus to separate the product. The resin which was most commonly used was Dowex 50X8-400. The solvent which was most commonly used for elution was water. Another method for separation of the N-phosphonomethylglycine was crystallization from the reaction mixture. In the alkaline reactions, the solvent could be removed and the trisodium salt of N-phosphonomethylglycine could be recovered.

The following examples serve to further illustrate this invention and are not intended to be a limitation on the scope of the invention. Examples 1-6 illustrate the preparation of the novel compounds of Formula II while the remaining examples illustrate the novel preparation of N-phosphonomethylglycine and derivatives.

EXAMPLE 1

To a stirred mixture of 12.8 g (0.10 mol) of N-(2-cyanoethyl)glycine and 13.8 g (0.10 mol) of diethylphosphite in 50 mL of water was added 7.5 mL of a 40% (w/v) formaldehyde solution all at once. The mixture was stirred for 18 hours during which time it had become a solution. The solvent was then removed under reduced pressure leaving a residue. This material was determined to consist mainly of N-(2-cyanoethyl)-N-(diethoxyphosphinyl)methyl]glycine.

To the residue was added 50 mL of concentrated hydrobromic acid. The resulting solution was then heated at reflux for 48 hours. The solvent was removed under reduced pressure until about 75 mL remained. Upon cooling, a precipitate appeared which was filtered and washed with cold ethanol. This solid consisted mainly of ammonium bromide.

The filtrate was then taken and the majority of the solvent was removed under reduced pressure. The remainder was then chromatographed on Dowex 50X8-400 ion exchange resin using water as the eluent. The major fraction contained 12.6 g (52%) of a white solid which was identified as N-(2-carboxyethyl)-N-phosphonomethylglycine on the basis of the following characteristics: mp 214° C. (d); $^1$H nmr (D$_2$O, NaOD, DSS, 90MHz) $\delta$2.46(t, J=7.5 Hz, 2H), 2.74(d, J=11.0 Hz, 2H), 3.08(t, J=7.5 Hz, 2H), 3.51(s, 2H); $^{31}$P nmr(D$_2$O, NaOD, 100MHz) $\delta$6.88.

EXAMPLE 2

To a well stirred mixture of 25.6 g (0.20 mol) of N-(2-cyanoethyl)glycine and 27.6 g (0.20 mol) of diethylphosphite in 100 mL of water was added 15.0 mL (0.20 mol) of a 40% (w/v) formaldehyde solution. The mixture was stirred for 24 hours during which time it became a solution. Then the solvent was removed under reduced pressure giving an oil. The oil was chromatographed on Dowex 50X8-400 ion exchange resin using water as the eluent. The ma]or fraction contained 42.6 g (77%) of an oil which was identified as N-(2-cyanoethyl)-N-[(diethoxyphosphinyl)methyl]glycine on the basis of the following characteristics: $^1$H nmr (D$_2$O, DSS, 90MHz) $\delta$1.33(t, J=7.5 Hz, 6H), 2.71(t, J=6.0 Hz, 2H), 3.16(t, J=6.0 Hz, 2H), 3.35(d, J=10.5 Hz, 2H), 3.68(s, 2H), 4.20(pent, J=7.5 Hz, 4H); $^{31}$P nmr (D$_2$O, 100MHz) $\delta$24.3; m/e 278, 194, 141, 125, 97, 83.

Anal. Calcd. for C$_{10}$H$_{19}$N$_2$O$_5$P: C, 43.17; H, 6.88; N, 10.07. Found: C, 42.92; H, 6.91; N, 10.01.

EXAMPLE 3

To a stirred solution of 6.43 g (0.023 mol) of the diethyl phosphorous ester of N-(2-cyanoethyl)-N-[(diethox-yphosphinyl)methyl]glycine in 100 mL of water was added 34.7 g (0.11 mol) of barium hydroxide hydrate. The reaction mixture was refluxed for 18 hours and then cooled. To this was added 6 mL of concentrated sulfuric acid dropwise. To the white emulsion was added diatomaceous earth, and this was then filtered through a sintered glass funnel. The filtrate was taken, and the solvent was removed under reduced pressure giving 4.04 g (73%) of a solid which was identified as N-(2-carboxyethyl)-N-phosphonomethylglycine.

EXAMPLE 4

To a well stirred solution of 2.78 g (0.10 mol) of N-(2-cyanoethyl)-N-[(diethoxyphosphinyl)methyl]glycine in 20 mL of water was added 0.80 g (0.20 mol) of sodium hydroxide. The solution was stirred for 24 hours at room temperature and then chromatographed on Dowex 50X8-400 ion exchange resin using water as the eluent. The ma]or fraction contained 1.71 g (68%) of a white solid which was identified as N-(2-cyanoethyl)-N-[(ethoxyhydroxyphosphinyl)methyl]glycine on the basis of the following characteristics: mp 165° C. (d); $^1$H nmr (D$_2$O, TSP, 90MHz) $\delta$1.30(t, J=7.5 Hz, 3H), 3.13(t, J=7.5 Hz, 2H), 3.54(d, J=12.0 Hz, 2H), 3.86(t, J=7.5 Hz, 2H), 3.98(t, J=7.5 Hz, 2H), 4.32(s, 2H); $^{31}$P nmr (D$_2$O, 0100MHz) $\delta$8.57.

Anal. Calcd. for C$_8$H$_{15}$N$_2$O$_5$P: C, 38.41; H, 6.04; N, 11.20; P, 12.38. Found: C, 38.36; H, 5.85; N, 11.09; P, 12.63.

EXAMPLE 5

A stirred solution containing 12.1 g (0.044 mol) of N-(2-cyanoethyl)-N-[(diethoxyphosphinyl)methyl]glycine in 100 mL of water was heated at reflux for 90 hours. Upon cooling to room temperature, a precipitate appeared which was collected and dried. There was present 7.8 g (81%) of a solid which was recrystallized from water/ethanol solution and identified as N-(2-cyanoethyl)-N-phosphonomethylglycine on the basis of the following characteristics: mp 195° C. (d); $^1$H nmr (D$_2$O, NaOD, DSS, 90MHz) $\delta$2.59(d, J=11.5 Hz, 2H), 2.66(t, J=7.0 Hz, 2H), 3.03(t, J=7.0 Hz, 2H), 3.30(s, 2H).

Anal. Calcd. for C$_6$H$_{11}$N$_2$O$_5$P: C, 32.44; H, 4.99; N, 12.61; P, 13.94. Found: C, 31.60; H, 5.12; N, 12.49; P, 14.08.

It was shown that in the remainder of the material there was present N-phosphonomethylglycine.

EXAMPLE 6

In a three neck round bottom flask equipped with an addition funnel, a reflux condenser, and a stir bar was added 50 mL of water, 50 mL of concentrated hydrochloric acid, and 10.7 g (0.13 mol) of phosphorous acid. The solution was stirred and heated at reflux and then treated with 18.3 g (0.10 mol) of N-(2-carboxyethyl)glycine. Then 9.8 mL of a 40% (w/v) formaldehyde solution was added dropwise over 30 minutes. Heating was continued an additional 60 minutes. The solvent was then removed under reduced pressure until only a few mL remained. This was allowed to sit at 5° C. during which time a precipitate formed. This solid was filtered, washed with ethanol, and dried. The solvent was removed from the filtrate under reduced pressure. The residue was chromatographed on Dowex 50X8-400 ion exchange resin using water as the eluent. Combined with the initial precipitate, the ma3or fraction gave a total of 12.7 g (52%) of N-(2-carboxyethyl)-N-phosphonomethylglycine.

EXAMPLE 7

In a three neck round bottom flask equipped with a reflux condenser, a thermometer, and a stir bar was added 4.82 g (0.020 mol) of N-(2-carboxyethyl)-N-phosphonomethylglycine, 4.0 g (0.10 mo) of sodium hydroxide, and 100 mL of water. The solution was stirred and heated at 103° C. for 114 hours. The solvent was then removed under reduced pressure until about 50 mL remained. The insoluble material was removed by filtration, and the filtrate was chromatographed on Dowex 50X8-400 ion exchange resin using water as the eluent. The minor fraction contained 1.19 g (25%) of a solid which was identified as the starting material. The major fraction contained 2.07 g (61%) of a solid which was identified as glyphosate on the basis of the following characteristics: '$^1$H nmr (D$_2$O, NaOD, DSS, 90MHZ) $\delta$2.53 (d, J=12.5 HZ, 2H), 3.22(s, 2H).

EXAMPLE 8

A stirred solution containing 6.5 g (0.023 mol) of the N-(2-cyanoethyl)-N-[(diethoxyphosphinyl)methyl]glycine in 50 mL of concentrated hydrochloric was heated at reflux for 12 hours. The solvent was then removed under reduced pressure giving a white solid which was identified as glyphosate. The material was recrystallized from water giving 3.62 g (92%) of the dry solid.

EXAMPLE 9

In a Parr bomb reactor was placed 1.2 g (0.0050 mol) of N-(2-carboxyethyl)-N-phosphonomethylglycine, 1.1 g (0.0275 mol) of sodium hydroxide, and 60 mL of water. The reactor was sealed and purged with nitrogen and then sealed. The reaction mixture was stirred and heated to 150° C. and kept there for 6 hours. During this time, the pressure in the bomb was $4.15 \times 10^5$ N/m². After cooling, the bomb was opened, and the solvent was removed under reduced pressure until about 15 mL remained. This was chromatographed on Dowex 50X8-400 ion exchange resin using water as the eluent. The major fraction gave 0.77 g (91%) of a solid which was identified as glyphosate.

EXAMPLE 10

In a round bottom flask with an efficient stirrer was placed 2.50 g of N-(2-cyanoethyl)-N-phosphonomethylglycine. This material was heated at 175° C. for 30 minutes. The flask was then cooled and the solid material was dissolved in sodium hydroxide solution. This was then chromatographed on Dowex 50X8-400 ion exchange resin using water as the eluent. The minor component contained 0.40 g (16%) of a solid which was identified as starting material, while the major fraction contained 1.08 g (64%) of a white solid which was identified as glyphosate.

EXAMPLE 11

In a flask equipped with an efficient stirrer was added 2.50 g (0.010 mol) of N-(2-cyanoethyl)-N-phosphonomethylglycine and 20 mL of decane. The mixture was stirred at 175° C. for 2 hours. The solvent was then removed under reduced pressure. The residue was then analyzed by nmr spectroscopy and found to contain glyphosate.

EXAMPLE 12

In a three neck round bottom flask equipped with a reflux condenser, a thermometer, and a stir bar was added 3.6 g (0.0150 mol) of N-(2-carboxyethyl)-N-phosphonomethylglycine and 100 mL of water. The reaction mixture was heated at 100° C. for 90 hours. The solvent was then removed under reduced pressure, and the residue was dissolved in 15 mL of water and chromatographed on Dowex 50X8-400 ion exchange resin using water as the eluent. The minor fraction contained 0.61 g (17%) of a solid which was identified as the starting material. The major fraction contained 1.69 g (67%) of a solid which was identified as glyphosate.

EXAMPLE 13

In a round bottom flask equipped with a stir bar was added 2.50 g (0.010 mol) of N-(2-cyanoethyl)-N-phosphonomethylglycine, 1.50 g (0.010 mol) of sodium iodide, and 50 mL of water. The solution was then stirred and heated at reflux for 48 hours. The solvent was then removed until about 10 mL remained, and this was chromatographed on a Dowex 50X8-400 ion exchange resin using water as the eluent. The minor component contained 0.50 g (20%) of the starting material. The major fraction contained 1.34 g (79%) of glyphosate.

EXAMPLE 14

In a round bottom flask equipped with a stir bar was added 2.50 g (0.010 mol) of N-(2-cyanoethyl)-N-phosphonomethylglycine, 4.65 g (0.050 mol) of aniline, and 100 mL of water. The mixture was stirred vigorously and heated at reflux for 24 hours. The solvent was then removed until a few mL remained, and this was chromatographed on Dowex 50X8-400 ion exchange resin using water as the eluent. The only fraction contained 1.63 g (96%) of a solid which was identified as glyphosate.

Although this invention has been described with respect to specific modifications, the details thereof are not to be construed as limitations for it will be apparent that various equivalents, changes, and modifications may be resorted to without departing from the spirit and scope thereof, and it is understood that such equivalent embodiments are intended to be included herein.

What is claimed is:

1. A process for the preparation of N-phosphonomethylglycine, which comprises the step of dealkylating a compound represented by the formula

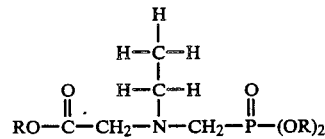

wherein E is selected from the group consisting of carboxyl, carboxylate anion, ethyl carboxylate, and methyl carboxylate, and each R is selected from the group consisting of hydrogen, lower alkyl, aryl and a salt-forming cation, by contacting the compound at a temperature between about 5° C. and about 300° C. with an acid selected from the group consisting of hydroiodic acid, hydrobromic acid, hydrochloric acid, hydrofluoric acid, hydrogen sulfide, nitric acid, nitrous acid, percholoric acid, picric acid, phosphoric acid, pyrophosphoric acid, sulfanilic acid, sulfurous acid, sulfuric acid, and trifluoroacetic acid.

2. A process as set forth in claim 1 wherein the acid is selected from the group consisting of hydrochloric, hydrobromic and sulfuric, and the temperature is from about 90° C. to about 150° C.

3. A process as set forth in claim 2 wherein E is carboxyl.

4. A process as set forth in claim 2 wherein E is a carboxylate anion.

5. A process as set forth in claim 4 wherein the cation to E is sodium of potassium.

6. A process for the preparation of N-phosphonomethylglycine, which comprises the step of dealkylating a compound represented by the formula

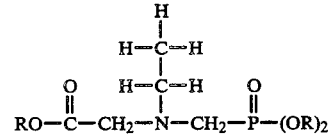

wherein E is selected from the group which consists of carboxyl, carboxylate anion, ethyl carboxylate and methyl carboxylate, and each R is selected from the group consisting of hydrogen, lower alkyl, aryl, and a salt-forming cation, by contacting the compound at a temperature between about 5° C. and about 300° C. with a base selected from the group which consists of alkali metal hydroxides, alkaline earth metal hydroxides, alkali metal carbonates, alkaline earth metal carbonates, alkali metal bicarbonates, ammonia, alkyl amines, aryl amines, and alkali metal alkoxides.

7. A process as set forth in claim 6 wherein the base is an alkali metal hydroxide and the temperature is between about 50° C. and 300° C.

8. A process for the preparation of N-phosphonomethylglycine, which comprises the step of dealkylating a compound represented by the formula

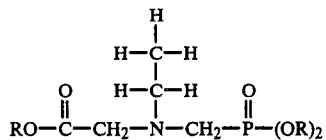

wherein E is selecteed from the group consisting of carboxyl, carboxylate anion, ethyl carboxylate and methyl carboxylate, and each R is selected from the group consisting of hydrogen, lower alkyl, aryl, and a salt-forming cation, by heating the compound to a temperature sufficient to dealkylate the compound.

9. A process of claim 8 wherein the temperature is about 175° C. or higher.

* * * * *

UNITED STATES PATENT AND TRADEMARK OFFICE
CERTIFICATE OF CORRECTION

PATENT NO. : 4,650,613
DATED : March 17, 1987
INVENTOR(S) : Mitchell J. Pulwer, Van R. Gaertner It is certified that error appears in the above-identified patent and that said Letters Patent are hereby corrected as shown below:

Claims 1, 6, and 8, the formula in each claim should read as follows:

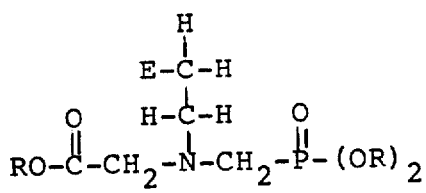

column 5, Example 2, line 29, the word <u>mag or</u> should be "major".

column 6, Example 4, line 2, the number is shown as <u>0100MH$_z$</u>. It should be "100MH$_z$".

column 6, Example 6, line 43, the word is shown as <u>ma3or</u>. It should be "major".

column 6, Example 7, line 51, the word is shown as <u>mo</u>. It should be "mol".

UNITED STATES PATENT AND TRADEMARK OFFICE
CERTIFICATE OF CORRECTION

PATENT NO. : 4,650,613

DATED : March 17, 1987

INVENTOR(S) : Mitchell J. Pulwer, Van R. Gaertner

It is certified that error appears in the above-identified patent and that said Letters Patent is hereby corrected as shown below:

Column 7, Example 9, line 7, the word is shown as plaoed. It should be "placed".

Signed and Sealed this

Twentieth Day of October, 1987

Attest:

DONALD J. QUIGG

Attesting Officer

Commissioner of Patents and Trademarks